United States Patent [19]

Bijwaard et al.

[11] 4,385,193

[45] May 24, 1983

[54] PROCESS FOR THE PREPARATION OF MIDDLE DISTILLATES

[75] Inventors: Henricus M. J. Bijwaard; Michael A. M. Boersma; Swan T. Sie, all of Amsterdam, Netherlands

[73] Assignee: Shell Oil Company, Houston, Tex.

[21] Appl. No.: 270,960

[22] Filed: Jun. 8, 1981

[30] Foreign Application Priority Data

Dec. 6, 1980 [NL] Netherlands .......................... 8003313

[51] Int. Cl.³ .............................................. C07C 1/04
[52] U.S. Cl. ..................................... 585/310; 585/319; 585/322; 585/408; 585/469; 585/638; 252/459; 252/460; 518/711; 518/715; 518/721
[58] Field of Search ............... 518/721, 715, 713, 714; 585/408, 418, 319, 322, 640, 310

[56] References Cited

U.S. PATENT DOCUMENTS

| | | | |
|---|---|---|---|
| 2,791,583 | 5/1957 | Weik | 585/408 X |
| 3,725,495 | 4/1973 | Wrisberg et al. | 585/418 X |
| 4,011,275 | 3/1977 | Zahner | 585/418 X |
| 4,044,064 | 8/1977 | Milstein et al. | |
| 4,052,477 | 10/1977 | Irelano et al. | 585/319 X |
| 4,080,397 | 3/1978 | Derr et al. | |
| 4,086,262 | 4/1978 | Chang et al. | 518/715 X |
| 4,207,248 | 6/1980 | Butter et al. | 518/715 OR |
| 4,208,305 | 6/1980 | Kowwenhoven et al. | 518/715 X |
| 4,263,141 | 4/1981 | Möuer et al. | 585/310 X |
| 4,273,724 | 6/1981 | Kugler et al. | 518/715 |

*Primary Examiner*—Delbert E. Gantz
*Assistant Examiner*—A. Pal
*Attorney, Agent, or Firm*—John M. Duncan; Ronald R. Reper

[57] ABSTRACT

Middle distillate hydrocarbons are produced from feed mixtures of carbon monoxide and hydrogen by contacting said feed at elevated temperature and pressure in a first stage with certain impregnated catalysts and contacting at least the middle distillate fraction of the product of the first stage in the presence of hyrogen with a catalyst containing at least one metal having hydrogenation activity supported on a porous carrier.

18 Claims, No Drawings

4,385,193

PROCESS FOR THE PREPARATION OF MIDDLE DISTILLATES

BACKGROUND OF THE INVENTION

The invention relates to a process for the preparation of middle distillates from a mixture of carbon monoxide and hydrogen.

The preparation of hydrocarbons from an $H_2/CO$ mixture by contacting said mixture at elevated temperature and pressure with a catalyst is known in the literature as the Fischer-Tropsch hydrocarbon synthesis process. Catalysts frequently used for this purpose contain one or more metals of the iron group together with one or more promoters and sometimes a carrier material. The preparation of Fischer-Tropsch catalysts can in principle be carried out by any of three methods, namely by precipitation, melting or impregnation. Both the precipitation route and the melting route are not very attractive preparation methods for the Fischer-Tropsch catalysts since their reproducibility is low. The precipitation route is moreover very time-consuming, and the melting route requires much energy. Also, the catalytic properties of the catalysts prepared by melting and precipitation, particularly activity and stability, are often not entirely satisfactory. A much more attractive preparation method for the Fischer-Tropsch catalysts is the impregnation route. This is simple to carry out, yields well-reproducible results and generally leads to catalysts having high activity and stability.

Applicants have carried out an extensive investigation into the preparation of hydrocarbons from $H_2/CO$ mixtures using Fischer-Tropsch catalysts prepared by impregnation. This investigation revealed that the behavior of these catalysts in said conversion greatly depends on the following factors:

(1) the nature of the metal of the iron group and the load used,
(2) the nature of the promoter and the load used,
(3) the nature of the carrier and
(4) the temperature treatment used.

It was further found that the use of these catalysts usually results in a product having a very broad molecular weight distribution, however, only a small part of said product consists of middle distillates. In addition to the yield, the pour point of said middle distillates is also unsatisfactory. In this connection the direct conversion of $H_2/CO$ mixtures by the Fischer-Tropsch process is a not very attractive route for the preparation of middle distillates on a technical scale.

Further investigation by the Applicants into the preparation of middle distillates from $H_2/CO$ mixtures revealed that a valuable product for middle distillate is obtained with the use of certain catalysts.

SUMMARY OF THE INVENTION

The present patent application therefore relates to a process for the preparation of middle distillates from a feed mixture of carbon monoxide and hydrogen, which comprises contacting an $H_2$- and CO-containing feed in a first stage at a temperature in the range of 125°–350° C. and pressure in the range of 1–150 bar with a first stage catalyst (Co-impregnation catalyst) containing 10–40 parts by weight of cobalt and 0.25–5 parts by weight of zirconium, titanium or chromium per 100 parts by weight of silica, and prepared by impregnating a silica carrier with one or more aqueous solutions of salts of cobalt and zirconium, titanium or chromium, followed by drying the composition, calcining at 350°–700° C. and reducing at 200°–350° C., with the proviso that if the feed has an $H_2/CO$ molar ratio of less than 1.5, water is added to said feed and that in said first stage the Co-impregnation catalyst is used in combination with a CO-shift catalyst, and contacting at least a suitable distillate fraction of the reaction product of the first stage in a second stage in the presence of hydrogen at an elevated temperature and pressure with a catalyst containing at least one metal with hydrogenation activity supported on a porous carrier.

DESCRIPTION OF PREFERRED EMBODIMENTS

The term "middle distillates" in this patent application refers to hydrocarbon mixtures boiling in the temperature range which mainly corresponds with that of the kerosine and gasoil fractions obtained in the conventional atmospheric distillation of crude oil. In said distillation the following fractions are consecutively separated from the crude oil: one or more gasoline fractions with a boiling range between 30° and 200° C., one or more kerosine fractions with a boiling range between 140° and 300° C. and one or more gasoil fractions with a boiling range between 180° and 370° C.

The catalysts employed in the first stage according to the invention are prepared by the impregnation route. Briefly, the impregnation route amounts to impregnating a porous carrier with one or more aqueous solutions of salts of one or more metals of the iron group and of one or more promoters, followed by drying, calcining and reducing the composition. As promoters for the catalysts prepared by impregnation, many elements are suitable, such as alkali metals, alkaline earth metals, metals of Group VIB, Ti, Zr, Th, V, Mn and Cu. As carrier materials for the catalysts prepared by impregnation both amorphous and crystalline materials are suitable. Suitable carriers are, for example, silica, alumina, zirconia, thoria, boria and combinations thereof, such as silica-alumina and silica-magnesia, and zeolites such as mordenite, faujasite and zeolite omega.

It has been found that in the conversion of $H_2/CO$ mixtures with the use of catalysts prepared by impregnation, a product is obtained which is very valuable for the preparation of middle distillates, if the catalysts contain 10–40 parts by weight of cobalt and 0.25–5 parts by weight of zirconium, titanium or chromium per 100 parts by weight of silica and have been calcined at a temperature of 350°–700° C. and reduced at a temperature of 200°–350° C. For it has been found that the high-boiling part of the product thus obtained can be converted in high yield into middle distillates by a catalytic hydrotreatment. The feed chosen for hydrotreatment is at least the part of the reaction product the initial boiling point of which is higher than the final boiling point of the heaviest middle distillate required as final product. The hydrotreatment which is characterized by a very low hydrogen consumption yields middle distillates having a considerably better pour point than those obtained in the direct conversion of an $H_2/CO$ mixture by the Fischer-Tropsch process.

For brevity's sake catalysts containing 10–40 parts by weight of cobalt and 0.25–5 parts by weight of zirconium, titanium or chromium per 100 parts by weight of silica and prepared by impregnating a silica carrier with one or more aqueous solutions of salts of cobalt and zirconium, titanium or chromium, followed by drying the composition, calcining at 350°–700° C. and reducing at 200°–350° C., will be further referred to in this patent application as "Co-impregnation catalysts".

If the feed to be converted over the Co-impregnation catalyst has an $H_2/CO$ molar ratio of less than 1.5, water has to be added to said feed and the CO-impregnation catalyst must be used in combination with a CO-shift catalyst.

If the feed for the first stage of the process according to the invention has an $H_2/CO$ molar ratio of less than 1.5, water has to be added to this feed and the Co-impregnation catalyst must be used in combination with a CO-shift catalyst. Preference is given to the use of CO-shift catalysts containing copper and zinc in which the Cu/Zn atomic ratio lies between 0.25 and 4.0. The excellent properties of the Co-impregnation catalysts used in the first stage of the process according to the invention, which catalysts can among other things be used at substantially higher pressures than the usual Fischer-Tropsch cobalt catalysts, enable a reaction product obtained by contacting an $H_2$- and CO-containing feed to which water is added with a CO-shift catalyst, to be converted over the CO-impregnation catalyst without $CO_2$ being removed from said product. Feeds with an $H_2/CO$ molar ratio of less than 1.5 and, if desired, also feeds having an $H_2/CO$ molar ratio of at least 1.5 can also be processed in the first stage of the process of the invention by contacting them after the addition of water with either a catalyst bed built up of several layers of consecutively a CO-shift catalyst and a Co-impregnation catalyst, or a physical mixture of a CO-shift catalyst and a Co-impregnation catalyst.

If in the process according to the invention, either as feed for the first stage or in the preparation of the feed for the first stage, use is made of an $H_2$- and CO-containing mixture to which water has been added and which mixture is contacted with a catalyst or catalyst combination possessing CO-shift activity, the quantity of water to be added to the $H_2$- and CO-containing mixture is mainly determined by the $H_2/CO$ molar ratio of the mixture, the CO-shift activity of the catalyst or catalyst combination and the desired $H_2/CO$ molar ratio of the product that is converted over Co-impregnation catalyst. The $H_2$- and CO-containing mixture used as feed for the first stage of the process according to the invention can, for example, be obtained by steam gasification of carbon-containing material. A very suitable feed for the first stage of the process according to the invention is a carbon monoxide- and hydrogen-containing fraction which can be separated from a reaction product that is obtained if an $H_2/CO$ mixture (1) with an $H_2/CO$ molar ratio of less than 2.0 is contacted with a bifunctional catalyst combination containing one or more metal components having catalytic activity for the conversion of an $H_2/CO$ mixture into acyclic hydrocarbons and/or acyclic oxygen-containing hydrocarbons and a crystalline silicate having the capacity of catalyzing the conversion of acyclic hydrocarbons and acyclic oxygen-containing hydrocarbons into aromatic hydrocarbons, with the proviso that if the $H_2/CO$ mixture (1) has an $H_2/CO$ molar ratio of less than 1.5, a trifunctional catalyst combination is used containing one or more metal components with catalytic activity for the conversion of an $H_2/CO$ mixture into acyclic hydrocarbons and/or acyclic oxygen-containing hydrocarbons, one or more metal components with CO-shift activity and a crystalline silicate having the capacity of catalyzing the conversion of acyclic hydrocarbons and acyclic oxygen-containing hydrocarbons into aromatic hydrocarbons. Said crystalline silicates are characterized in that they possess the following properties after one hour's calcination in air at 500° C.:

(a) thermally stable to a temperature above 600° C.,
(b) an X-ray powder diffraction pattern containing the four lines stated in Table A as strongest lines.

TABLE A

| d(Å) | Relative intensity |
|---|---|
| 11.1 ± 0.2 | VS |
| 10.0 ± 0.2 | VS |
| 3.84 ± 0.07 | S |
| 3.72 ± 0.06 | S | where the letters have the following meanings:
VS = very strong;
S = strong, and (c) in the formula representing the composition of the silicate expressed in moles of oxides and containing in addition to oxides of hydrogen, alkali metal and/or alkaline earth metal and silicon, one or more oxides of a trivalent metal A chosen from the group consisting of aluminum, iron, gallium, rhodium, chromium and scandium, the $SiO_2/A_2O_3$ molar ratio is more than 10.

The bi- and trifunctional catalyst combinations referred to above contain, in addition to metal components with catalytic activity, a crystalline metal silicate characterized by the properties stated in (a) to (c). Preference is given to a silicate containing only one of said metals and in particular to silicates containing as metal aluminum, iron or gallium. The complete X-ray powder diffraction pattern of a typical example of a silicate as described above is shown in Table B.

TABLE B

| d(Å) | Relative intensity | d(Å) | Relative intensity |
|---|---|---|---|
| 11.1 | 100 | 4.00 | 3 |
| 10.0 | 70 | 3.84 | 57 |
| 8.93 | 1 | 3.72 | 31 |
| 7.99 | 1 | 3.64 | 10 |
| 7.42 | 1 | 3.44 | 5 |
| 6.68 | 7 | 3.34 | 3 |
| 6.35 | 11 | 3.30 | 5 |
| 5.97 | 18 | 3.25 | 2 |
| 5.70 | 7 | 3.05 | 5 |
| 5.56 | 10 | 2.98 | 12 |
| 5.35 | 2 | 2.96 | 3 |
| 4.98 | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |

Although the trifunctional catalyst combinations are described in the present patent application as catalyst combinations containing one or more metal components with catalytic activity for the conversion of an $H_2/CO$ mixture into acyclic hydrocarbons and/or acyclic oxygen-containing hydrocarbons and one or more metal components with CO-shift activity, this by no means implies that separate metal components each individually possessing one of the two catalytic functions must be present in the trifunctional catalyst combinations. It has in fact been found that metal components and combinations of metal components having catalytic activity for the conversion of an $H_2/CO$ mixture into substantially acyclic oxygen-containing hydrocarbons usually also have sufficient CO-shift activity, so that in this case it will usually suffice to introduce one metal component or one combination of metal components into the trifunctional catalyst combinations. Metal components and combinations of metal components having catalytic activity for the conversion of an $H_2/CO$ mixture into substantially acyclic hydrocarbons usually possess no or insufficient CO-shift activity. Consequently, when such metal components or metal component combinations are used in the trifunctional catalyst combinations one or more separate metal components with CO-shift activity must mostly be introduced into the catalyst combination.

The crystalline silicate-containing bi- and trifunctional catalyst combinations referred to above preferably consist of two or three separate catalysts that are indicated for the sake of convenience as catalysts X, Y and Z. Catalyst X is the catalyst containing the metal components with catalytic activity for the conversion of an $H_2/CO$ mixture into acyclic hydrocarbons and/or acyclic oxygen-containing hydrocarbons. Catalyst Y is the crystalline silicate. Catalyst Z is the catalyst containing the metal components with CO-shift activity. As explained in the foregoing, in the case of the trifunctional catalyst combinations the use of a catalyst Z can be dispensed with in a number of cases.

If as catalyst X use is made of a catalyst which is capable of converting an $H_2/CO$ mixture into substantially acyclic oxygen-containing hydrocarbons, preference is given to a catalyst capable of converting the $H_2/CO$ mixture into substantially methanol and/or dimethyl ether. Very suitable catalysts for this purpose are $ZnO-Cr_2O_3$ compositions, in particular such compositions in which the atomic percentage of zinc based on the sum of zinc and chromium is at least 60% and preferably 60–80%. If the catalyst X used is a $ZnO-Cr_2O_3$ composition, the use of a catalyst Z can be dispensed with in the trifunctional catalyst combinations.

The following iron catalysts are also very suitable as catalysts X:

(a) catalysts containing 30–75 parts by weight of iron and 5–40 parts by weight of magnesium per 100 parts by weight of alumina and prepared by impregnating an alumina carrier with one or more aqueous solutions of salts of iron and of magnesium followed by drying the composition, calcining at a temperature of 700°–1200° C. and reducing it. Particularly preferred are catalysts of this type that contain in addition to 40–60 parts by weight of iron and 7.5–30 parts by weight of magnesium, 0.5–5 parts by weight of copper as reduction promoter and 1–5 parts by weight of potassium as selectivity promoter per 100 parts by weight of alumina and which are calcined at 750°–850° C. and reduced at 250°–350° C.

(b) Catalysts containing 10–40 parts by weight of iron and 0.25–10 parts by weight of chromium per 100 parts by weight of silica and prepared by impregnating a silica carrier with one or more aqueous solutions of salts of iron and of chromium followed by drying and calcining the composition and reducing it at a temperature of 350°–750° C. Particular preference is given to catalysts of this type that contain in addition to 20–35 parts by weight of iron and 0.5–5 parts by weight of chromium, 1–5 parts by weight of potassium as selectively promoter and which are calcined at 350°–700° C. and reduced at 350°–500° C.

When the iron catalysts mentioned under (a) and (b) are used as catalyst X, the use of a catalyst Z can be dispensed with in the trifunctional catalyst combinations.

In the crystalline silicate-containing bi- and trifunctional catalyst combinations the catalysts X, Y and possibly Z are preferably present as a physical mixture. When a fixed catalyst bed is used, the bed can also be built up of alternating layers of particles of catalysts X, Y and possibly Z.

If in the process according to the invention the feed used for the first stage is a carbon monoxide- and hydrogen-containing fraction separated from the reaction product that can be obtained by contacting an $H_2/CO$ mixture (1) with the above-mentioned crystalline silicate-containing bi- or trifunctional catalyst combinations, for said purpose a fraction is preferably chosen such as is separated from a reaction product prepared under the following conditions: a temperature of 200°–500° C., in particular 250°–450° C., a pressure of 1–150 bar, in particular 5–100 bar, and a space velocity of 50–5000, in particular 300–3000 Nl of gas/l of catalyst/h.

Another very suitable feed for the first stage of the process according to the invention is a carbon monoxide- and hydrogen-containing fraction that can be separated from a reaction product that is obtained if an $H_2/CO$ mixture with an $H_2/CO$ molar ratio of less than 1.0 is contacted with an iron-containing bifunctional catalyst or catalyst combination possessing CO-shift activity in addition to activity for the conversion of an $H_2/CO$ mixture into substantially hydrocarbons. For this purpose use is preferably made of a bifunctional catalyst prepared by impregnation and containing iron on a carrier. Examples of such catalysts are the iron catalysts described in the foregoing under (a) and (b). If in the process according to the invention the feed for the first stage is a carbon monoxide- and hydrogen-containing fraction separated from the reaction product that can be obtained by contacting an $H_2/CO$ mixture (2) with the above-mentioned iron-containing bifunctional catalyst or catalyst combination, for said purpose a fraction is preferably chosen such as is separated from a reaction product prepared under the following conditions: a temperature of 200°–350° C. and in particular of 250°–350° C., a pressure of 10–70 bar and in particular of 20–50 bar and a space velocity of 500–5000 and in particular of 500–2500 Nl of gas/l of catalyst/h.

If in the process according to the invention the feed used for the first stage is an $H_2$- and CO-containing fraction separated from the reaction product obtained either by contacting an $H_2/CO$ mixture (1) with the above-mentioned crystalline silicate-containing bi- or trifunctional catalyst combinations, or by contacting an $H_2/CO$ mixture (2) with the above iron-containing bifunctional catalysts or catalyst combinations, said fraction can contain, in addition to carbon monoxide and hydrogen, also other components of the reaction product. It is possible, for example, to use as feed for the first stage of the process according to the invention the $C_2$ and lighter ($C_{2-}$) fraction or $C_{4-}$ fraction of the reaction product or even the complete reaction product. The abovementioned $H_2/CO$ mixtures (1) and (2) are preferably obtained by steam-gasification of coal at a temperature of 900°–1500° C. and a pressure of 10–100 bar.

The first step of the process according to the invention is preferably carried out at a temperature of 125°–350° C., in particular 175°–275° C., and a pressure of 1–150 bar, in particular 5–100 bar.

In the process according to the invention at least that part of the reaction product of the first stage the initial boiling point of which is higher than the final boiling point of the heaviest middle distillate required as final product must be subjected to a catalytic hydrotreatment in a second stage. The catalytic hydrotreatment is carried out by contacting the relevant fraction of the reaction product of the first stage with a catalyst containing one or more metals with hydrogenation activity on a carrier, at elevated temperature and pressure and in the presence of hydrogen. Examples of suitable catalysts are sulphidic (sulfided) catalysts containing nickel and/or cobalt and moreover molybdenum and/or tungsten on a carrier such as alumina or silica-alumina. In the catalytic hydrotreatment use is preferably made of a catalyst containing one or more noble metals of Group VIII on a carrier. The quantity of noble metal present on the carrier may vary within wide limits, but is usually 0.05–5% by weight. The noble metals of Group VIII, which may be supported on the carrier, are platinum, palladium, rhodium, ruthenium, iridium and osmium, of which platinum is preferred. If desired, two or more of said metals may be present in the catalysts. The quantity of noble metal of Group VIII present in the catalyst is preferably 0.1–2% by weight and in particular 0.2–1% by weight. Examples of suitable carriers for the noble metal catalysts are amorphous oxides of the elements of Groups II, III and IV, such as silica, alumina, magnesia, zirconia as well as mixtures of said oxides such as silica-alumina, silica-magnesia and silica-zirconia and zeolitic materials such as mordenite and faujasite. As carriers for the noble metal catalysts alumina and silica-alumina are preferred. A very suitable noble metal catalyst for the present purpose is a catalyst containing one or more noble metals of Group VIII on a carrier, which carrier comprises 13–15% by weight of alumina, the remainder being silica. Suitable conditions for carrying out the catalytic hydrotreatment are a temperature of 175°–400° C., a hydrogen partial pressure of 10–250 bar, a space velocity of 0.1–5 kg·l$^{-1}$·h$^{-1}$ and a hydrogen/oil ratio of 100–5000 Nl·kg$^{-1}$. The catalytic hydrotreatment is preferably carried out under the following conditions: a temperature of 250°–350° C., a hydrogen partial pressure of 25–150 bar, a space velocity of 0.25–2 kg·l$^{-1}$·h$^{-1}$ and a hydrogen/oil ratio of 250–2500 Nl·kg$^{-1}$. By making a correct choise of the catalyst and the treating conditions in the second stage it is possible in the process according to the invention to prepare, in addition to middle distillate, high-viscosity index lubricating oil from a heavy fraction of the product of the first stage.

The invention will now be illustrated with reference to the following Example.

EXAMPLE

In the investigation use was made of the following catalysts:

Catalyst 1

Co/Zr/SiO$_2$ catalyst containing 25 parts by weight of cobalt and 1.8 parts by weight of zirconium per 100 parts by weight of silica, which was prepared by impregnating a silica carrier with an aqueous solution containing a cobalt and a zirconium salt, followed by drying the composition, calcining at 500° C. and reducing at 280° C.

Catalyst 2

Pt/SiO$_2$-Al$_2$O$_3$ catalyst, containing 0.82 parts by weight of platinum per 100 parts by weight of carrier, which carrier consisted of 14.6% by weight of alumina and 85.4% by weight of silica.

Catalyst 3

Cu/Zn/Al$_2$O$_3$ catalyst having a Cu/Zn atomic ratio of 0.55.

Catalyst 4

ZnO-Cr$_2$O$_3$ catalyst in which the atomic percentage of zinc, based on the sum of zinc and chromium, was 70%.

Catalyst 5

A crystalline silicate A was prepared by heating a mixture of SiO$_2$, NaOH, (C$_3$H$_7$)$_4$NOH and Fe(NO$_3$)$_3$ in water with the molar composition

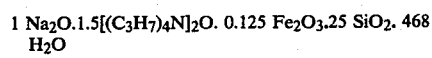

at 150° C. for 6 hours in an autoclave under autogenous pressure. After the reaction mixture had been cooled, the silicate A formed was filtered off, washed with water until the pH of the washing water was about 8, dried at 120° C. and calcined at 500° C. Silicate A had the following properties:
 (a) thermally stable to a temperature above 800° C.,
 (b) an X-ray powder diffraction pattern mainly as stated in Table B,
 (c) an SiO$_2$/Fe$_2$O$_3$ molar ratio of 200.

Catalyst 5 was prepared from silicate A by boiling silicate A with 1.0 molar NH$_4$NO$_3$ solution, washing with water, reboiling with 1.0 molar NH$_4$NO$_3$ solution, washing, drying and calcining.

Catalyst 6

Fe/Mg/Cu/K/Al$_2$O$_3$ catalyst containing 50 parts by weight of iron, 20 parts by weight of magnesium, 2.5 parts by weight of copper and 4 parts by weight of potassium per 100 parts by weight of alumina, which catalyst had been prepared by impregnating an alumina carrier with an aqueous solution containing an iron, magnesium, copper and potassium salt, following by drying the composition, calcining at 800° C. and reducing at 325° C.

Catalyst Mixture I

Catalyst mixture I consisted of a layer of catalyst 3 and a layer of catalyst 1 in a volume ratio of 1:2.

Catalyst Mixture II

Catalyst mixture II consisted of a physical mixture of catalyst 4 and catalyst 5 in a volume ratio 2:1.

The catalysts 1, 2, 3 and 6 and the catalyst mixtures I and II were tested in the preparation of middle distillates from H$_2$– and CO– containing mixtures.

Experiment 1

An H$_2$/CO mixture with an H$_2$/CO molar ratio of 1.8 was passed through a 250-ml reactor containing a fixed catalyst bed consisting of 45 ml of catalyst 1, at a temperature of 220° C., a pressure of 30 bar and a space velocity of 500 Nl.l$^{-1}$·h$^{-1}$. The conversion of the H$_2$/CO mixture was 93% by volume. The reaction product prepared over catalyst 1 is indicated as product 1A.

Experiment 2

An H$_2$/CO mixture with an H$_2$/CO molar ratio of 0.5 as passed through a 50-ml reactor containing a fixed catalyst bed consisting of 10 ml of catalyst 3, with the addition of 268 ml of water/l of catalyst/h at a temperature of 220° C., a pressure of 30 bar and a space velocity of 1000 Nl.l$^{-1}$·h$^{-1}$. The reaction product prepared over catalyst 3, the $H_2/CO$ molar ratio of which was 2.0, was passed through a 50-ml reactor containing a fixed catalyst bed consisting of 27 ml of catalyst 1, at a temperature of 220° C., a pressure of 30 bar and a space velocity of 500 $Nl.l^{-1}.h^{-1}$. The conversion of the $H_2/CO$ mixture was 93% by volume.

The reaction product prepared over catalyst 1 is indicated as product 2A.

products 1A-5A is stated in Table C. Of each of the products 1A-5A the $C_5+$ fraction was passed through a 50-ml reactor containing a fixed catalyst bed consisting of 8 ml of catalyst 2, at a temperature of 345° C., a hydrogen partial pressure of 130 bar, a space velocity of 1.25 $l.l^{-1}.h^{-1}$ and a hydrogen/oil ratio of 2000 Nl/l. The reaction products prepared over catalyst 2 are indicated as products 1B-5B, which was determined in the same manner as that of products 1A-5A, is stated in Table C.

TABLE C

| Product No. | Product Composition, % By Wt | | | | | | | | | |
|---|---|---|---|---|---|---|---|---|---|---|
| | 1A | 1B | 2A | 2B | 3A | 3B | 4A | 4B | 5A | 5B |
| 150° C.− fraction | 4.2 | 6.9 | 4.3 | 7.0 | 6.3 | 9.0 | 19.3 | 22.3 | 10.1 | 13.2 |
| 150-250° C. fraction | 18.7 | 22.3 | 18.6 | 22.0 | 20.6 | 24.2 | 23.1 | 28.6 | 22.3 | 27.8 |
| 250-360° C. fraction | 24.9 | 44.7 | 25.0 | 44.6 | 27.0 | 46.6 | 18.6 | 32.0 | 23.1 | 39.3 |
| 360-400° C. fraction | 10.4 | 11.0 | 10.3 | 10.9 | 9.2 | 8.9 | 7.8 | 7.5 | 9.3 | 8.2 |
| 400° C.+ oil fraction | 3.1 | 10.6 | 3.1 | 10.8 | 2.9 | 9.0 | 2.3 | 6.2 | 2.8 | 6.8 |
| 400° C.+ paraffin fraction | 38.7 | 4.5 | 38.7 | 4.5 | 34.0 | 2.3 | 28.9 | 3.4 | 32.4 | 4.7 |

Experiment 3

An $H_2/CO$ mixture with an $H_2/CO$ molar ratio of 0.5 was passed through a 50-ml reactor containing a fixed catalyst bed consisting of 15 ml of catalyst mixture I, with the addition of 268 ml of water/l of catalyst/h at a temperature of 220° C., a pressure of 30 bar and a space velocity of 500 $Nl.l^{-1}.h^{-1}$. The conversion of the $H_2/CO$ mixture was 90% by volume. The reaction product prepared over catalyst mixture I is indicated as product 3A.

Experiment 4

An $H_2/CO$ mixture with an $H_2/CO$ molar ratio of 1.3 was passed through a 50-ml reactor containing a fixed catalyst bed consisting of 2.75 ml of catalyst mixture II, at a temperature of 375° C. and a pressure of 60 bar. The reaction product prepared over catalyst mixture II, the $H_2/CO$ molar ratio of which was 2.0, was passed through a 50-ml reactor containing a fixed catalyst bed consisting of 11.25 ml of the catalyst 1, at a temperature of 220° C. and a pressure of 60 bar. In this experiment the space velocity based on the total catalyst system (catalyst mixture II+catalyst 1) was 500 $Nl.l^{-1}.h$. The reaction product prepared over catalyst 1 is indicated as product 4A.

Experiment 5

An $H_2/CO$ mixture with an $H_2/CO$ molar ratio of 0.5 was passed through a 50-ml reactor containing a fixed catalyst bed consisting of 5 ml of catalyst 6, at a temperature of 280° C. and a pressure of 30 bar. The reaction product prepared over catalyst 6, the $H_2/CO$ molar ratio of which was 0.41, was passed through a 50-ml reactor containing a fixed catalyst bed consisting of 5 ml of catalyst mixture I, with the addition of 241 ml of water/l of catalyst/h at a temperature of 230° C. and a pressure of 30 bar. In this experiment the space velocity based on the total catalyst system (catalyst 6+catalyst mixture I) was 1000 $Nl.l^{-1}.h^{-1}$. The reaction product prepared over catalyst mixture I is indicated as product 5A.

The composition of products 1A-5A was determined by separating samples of these products by distillation into a 150° C.− fraction, a 150°-250° C. fraction, a 250°-360° C. fraction, a 360°-400° C. fraction and a 400° C.+ fraction and separating the latter fraction by cooling to −20° C. in the presence of a mixture of methyl ethyl ketone and toluene into a 400° C.+ oil fraction and a 400° C.+ paraffin fraction. The composition of the Some properties of three fractions of product 1B are stated below:

Fraction 150°–250° C.:
 smoke point >50 mm,
 cloud point −35° C.,
 pour point −32° C.
Fraction 250°–360° C.:
 cloud point −4° C.,
 pour point −1° C.,
 diesel index 102.
Oil fraction 400° C.+:
 Viscosity, kinematic 100° F. ($V_{K100}$) 31.3 cS,
 Viscosity, kinematic 210° F. ($V_{K210}$) 62.2 cS,
 Viscosity index VI 152.7.

What is claimed is:

1. A process for the preparation of a hydrocarbon mixture, a major proportion of which is middle distillates boiling in the temperature range between about 140° and about 370° C., from a feed mixture of carbon monoxide and hydrogen, which comprises contacting an $H_2$- and CO-containing feed in a first stage at a temperature in the range of 125°–350° C. and pressure in the range of 1–150 bar with a first stage fixed bed catalyst (Co-impregnation catalyst) containing 10–40 parts by weight of cobalt and 0.25–5 parts by weight of zirconium, titanium or chromium per 100 parts by weight of silica, said first stage catalyst having been prepared by impregnating a silica carrier with one or more aqueous solutions of salts of cobalt and zirconium, titanium or chromium, followed by drying the composition, calcining at 350°–700° C. and reducing at 200°–350° C., with the proviso that if the feed has an $H_2/CO$ molar ratio of less than 1.5, water is added to said feed and that in said first stage the Co-impregnation catalyst is used in combination with a CO-shift catalyst, and contacting at least a suitable distillate fraction of the reaction product of the first stage in a second stage in the presence of hydrogen at an elevated temperature and pressure with a fixed bed catalyst containing at least one metal with hydrogenation activity supported on a porous carrier.

2. A process as in claim 1 wherein water is added to the $H_2$- and CO-containing mixture feed to the first stage, and first contacts a CO-shift catalyst and then contacts a Co-impregnation catalyst without CO having been removed.

3. A process as in claim 1 wherein said $H_2$- and CO-containing feed mixture to which water has been added is contacted in the first stage with a catalyst bed which is either built up on several alternating layers of consecutively a CO-shift catalyst and a Co-impregnation catalyst, or said bed is a physical mixture of a CO-shift catalyst and a Co-impregnation catalyst.

4. A process as in claim 1 wherein the first stage is carried out at a temperature of 175°–275° C. and a pressure of 5–100 bar.

5. A process as in claim 1 wherein the second stage catalyst contains one or more noble metals of Group VIII supported on a carrier.

6. A process as in claim 5 wherein in the second stage a catalyst contains 0.1–2% by weight of one or more noble metals of Group VIII supported on a carrier comprising 13–15% by weight of alumina, the remainder consisting of silica.

7. A process as in claim 1 wherein the second stage is carried out at a temperature of 175°–400° C., a hydrogen partial pressure of 10–250 bar, a space velocity of 0.1–5 kg.l$^{-1}$·h$^{-1}$ and a hydrogen/oil ratio of 100–5000 Nl·kg$^{-1}$.

8. A process as in claim 1 wherein said feed for the first stage comprises an H$_2$- and CO-containing fraction which has been separated from a reaction product from a prior reaction, said prior reaction comprising contacting an H$_2$/CO mixture having an H$_2$/CO molar ratio of less than 2.0 with a bifunctional catalyst combination containing one or more metal components with catalytic activity for the conversion of an H$_2$/CO mixture into acyclic hydrocarbons and/or acyclic oxygen-containing hydrocarbons and a crystalline silicate, which silicate possesses the following properties after one hour's calcination in air at 500° C.:
 (a) thermally stable to a temperature above 600° C.,
 (b) an X-ray powder diffraction pattern containing the four lines stated in Table A in the specification as strongest lines,
 (c) in the formula representing the composition of the silicate expressed in moles of oxides and containing in addition to oxides of hydrogen, alkali metal and/or alkaline earth metal and silicon, one or more oxides of a trivalent metal A chosen from the group consisting of aluminum, iron, gallium, rhodium, chromium and scandium, the SiO$_2$/A$_2$O$_3$ molar ratio is more than 10, with the proviso that if the H$_2$/CO feed mixture has an H$_2$/CO molar ratio of less than 1.5, a trifunctional catalyst combination is used contained one or more metal components with catalytic activity for the conversion of an H$_2$/CO mixture into acyclic hydrocarbons and/or acyclic oxygen-containing hydrocarbons, one or more metal components with CO-shift activity and the crystalline silicate.

9. A process as in claim 8 wherein said crystalline silicate is selected from the group consisting of aluminum, iron or gallium silicates.

10. A process as in claim 8 wherein the trifunctional catalyst combination is composed of two separate catalysts X and Y, catalyst X possessing activity for the conversion of an H$_2$/CO mixture into acyclic hydrocarbons and/or acyclic oxygen-containing hydrocarbons as well as CO-shift activity and catalyst Y is the crystalline silicate.

11. A process as in claim 8 wherein as catalyst X is capable of converting an H$_2$/CO mixture into mainly methanol and/or dimethyl ether.

12. A process as in claim 8 wherein catalyst X contains 30–75 parts by weight of iron and 5–40 parts by weight of magnesium per 100 parts by weight of alumina and is prepared by impregnating an alumina carrier with one or more aqueous solutions of salts of iron and magnesium, followed by drying the composition, calcining at a temperature of 700°–1200° C. and, finally reducing.

13. A process as in claim 8 wherein catalyst X contains 10–40 parts by weight of iron and 0.25–10 parts by weight of chromium per 100 parts by weight of silica and is prepared by impregnating a silica carrier with one or more aqueous solutions of salts of iron and chromium, followed by drying the composition, calcining and reducing at a temperature of 350°–750° C.

14. A process as in claim 8 wherein said prior reaction is carried out at a temperature of 200°–500° C., a pressure of 1–150 bar and a space velocity of 50–5000 Nl of gas/l of catalyst/h.

15. A process as in claim 1 wherein said feed for the first stage comprises an H$_2$- and CO-containing fraction which has been separated from a reaction product of a prior reaction, said prior reaction comprising contacting an H$_2$/CO mixture having an H$_2$/CO molar ratio of less than 1.0 with an iron-containing bifunctional catalyst or catalyst combination possessing CO-shift activity in addition to activity for the conversion of an H$_2$/CO mixture into substantially hydrocarbons.

16. A process as in claim 15 wherein said prior reaction is carried out at a temperature of 200°–350° C., a pressure of 10–70 bar and a space velocity of 500–5000 Nl of gas/l of catalyst/h.

17. A process as in claim 8 wherein the H$_2$/CO feed mixture to said prior reaction are prepared by steam-gasification of coal at a temperature of 700°–1500° C. and a pressure of 10–1000 bar.

18. A process as in claim 1 wherein at least about 60 percent by weight of the hydrocarbon mixture product is middle distillates boiling in the temperature range between about 150° and about 360° C.

* * * * *